(12) United States Patent
Canon

(10) Patent No.: US 11,771,385 B1
(45) Date of Patent: Oct. 3, 2023

(54) SURGICAL OR EXAM TABLE THAT FACILITATES IMAGING DURING PROCEDURES

(71) Applicant: William Barry Canon, College Station, TX (US)

(72) Inventor: William Barry Canon, College Station, TX (US)

( * ) Notice: Subject to any disclaimer, the term of this patent is extended or adjusted under 35 U.S.C. 154(b) by 0 days.

(21) Appl. No.: 17/993,613

(22) Filed: Nov. 23, 2022

Related U.S. Application Data

(63) Continuation-in-part of application No. 17/576,777, filed on Jan. 14, 2022, now Pat. No. 11,534,116.

(60) Provisional application No. 63/141,337, filed on Jan. 25, 2021.

(51) Int. Cl.
   *A61B 6/00* (2006.01)
   *A61B 6/04* (2006.01)

(52) U.S. Cl.
   CPC .......... *A61B 6/4283* (2013.01); *A61B 6/0407* (2013.01)

(58) Field of Classification Search
   CPC ....... A61B 6/00; A61B 6/4283; A61B 6/0407; A61G 6/42
   See application file for complete search history.

(56) References Cited

U.S. PATENT DOCUMENTS

| | | | | |
|---|---|---|---|---|
| 3,967,128 A | * | 6/1976 | Smulewicz | A61B 6/0421 5/601 |
| 4,637,043 A | * | 1/1987 | Bauer | G03B 42/04 378/188 |
| 5,422,928 A | * | 6/1995 | Payne | A61B 6/0442 378/177 |
| 7,793,366 B2 | * | 9/2010 | Stoltzfus | A47C 17/40 5/907 |

\* cited by examiner

*Primary Examiner* — Fredrick C Conley
(74) *Attorney, Agent, or Firm* — Plager Schack LLP; Mark H. Plager; Naomi Mann

(57) ABSTRACT

A surgical or exam table includes a radiolucent patient support surface; and a shelf beneath the patient support surface, wherein an X-ray panel may be supported on said shelf for X-raying a human or animal subject resting on the support surface.

8 Claims, 4 Drawing Sheets

SURGICAL OR EXAM TABLE THAT FACILITATES IMAGING DURING PROCEDURES

RELATED APPLICATION

This application is a continuation-in-part of application Ser. No. 17/576,777, filed on Jan. 14, 2022, which claims benefit to U.S. Provisional Application No. 63/141,337 filed on Jan. 25, 2021, all of which are incorporated by reference herein in their entirety.

BACKGROUND

The embodiments herein relate generally to devices and methods for performing medical procedures.

X-raying a human or animal subject may be critical to medical treatment. However, movement of the subject might be inconvenient or even harmful during regular or emergency procedures, such as examinations and surgeries. Additionally, some facilities, such as veterinary and small clinics, may be ill equipped for whole body scanning. As such, an improved system is desirable.

SUMMARY

According to various embodiments, disclosed is a surgical or exam table, comprising a radiolucent or X-ray transparent support surface configured to support a patient, which enables placement of any X-ray detector panel underneath the support surface. In embodiments, the medical table may comprise a support member coupled to the X-ray transparent support surface, which supports the X-ray transparent support surface above ground level. In certain embodiments, the table may further comprise a shelf connected underneath the support surface, which supports the X-ray detector panel.

According to various embodiments, further disclosed is an X-ray imaging method comprising: providing an X-ray transparent support surface, the X-ray transparent patient support surface being elevated above a ground level and configured to support a patient; placing a patient on top of the X-ray transparent support surface; placing an X-ray detector member on a detector support member beneath the X-ray transparent support surface; and taking an X-ray of the patient by radiating X-rays through the patient and X-ray transparent support surface to expose the X-ray detector member beneath the X-ray transparent support surface.

According to various embodiments, further disclosed is an X-ray imaging method comprising: providing an X-ray transparent support surface; placing a patient on top of the X-ray transparent support surface; placing an X-ray detector member on a detector support member beneath the X-ray transparent support surface; and taking an X-ray of the patient by radiating X-rays through the patient and X-ray transparent support surface to expose the X-ray detector member beneath the X-ray transparent support surface, wherein the X-ray transparent support surface is rotationally coupled to a wall via a hinge connector, and is configured to fold into the wall for storage.

According to various embodiments, disclosed is a medical table comprising: an X-ray transparent support surface configured to support a patient; a hinge coupled to the X-ray transparent support surface, the hinge configured to pivotally couple the X-ray transparent support surface to a wall.

According to various embodiments, further disclosed is a medical table comprising: an X-ray transparent support surface configured to support a patient; a detector support member coupled to the X-ray transparent support member and providing a shelf beneath the X-ray transparent support member configured to hold an X-ray detector member, entire length of table, wherein the detector support member comprises a horizontal panel connected to the X-ray transparent support surface via a pair of vertical side panels, wherein the detector support member is space apart from the X-ray transparent support surface to form an unobstructed opening between the X-ray transparent support surface, the pair of vertical side panels, and the detector support member, said unobstructed opening extending along an entire length of the X-ray transparent support surface, and wherein the X-ray detector member can be inserted through said opening and supported on the detector support member such that the X-ray detector member is allowed full movement anywhere under X-ray transparent support surface.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
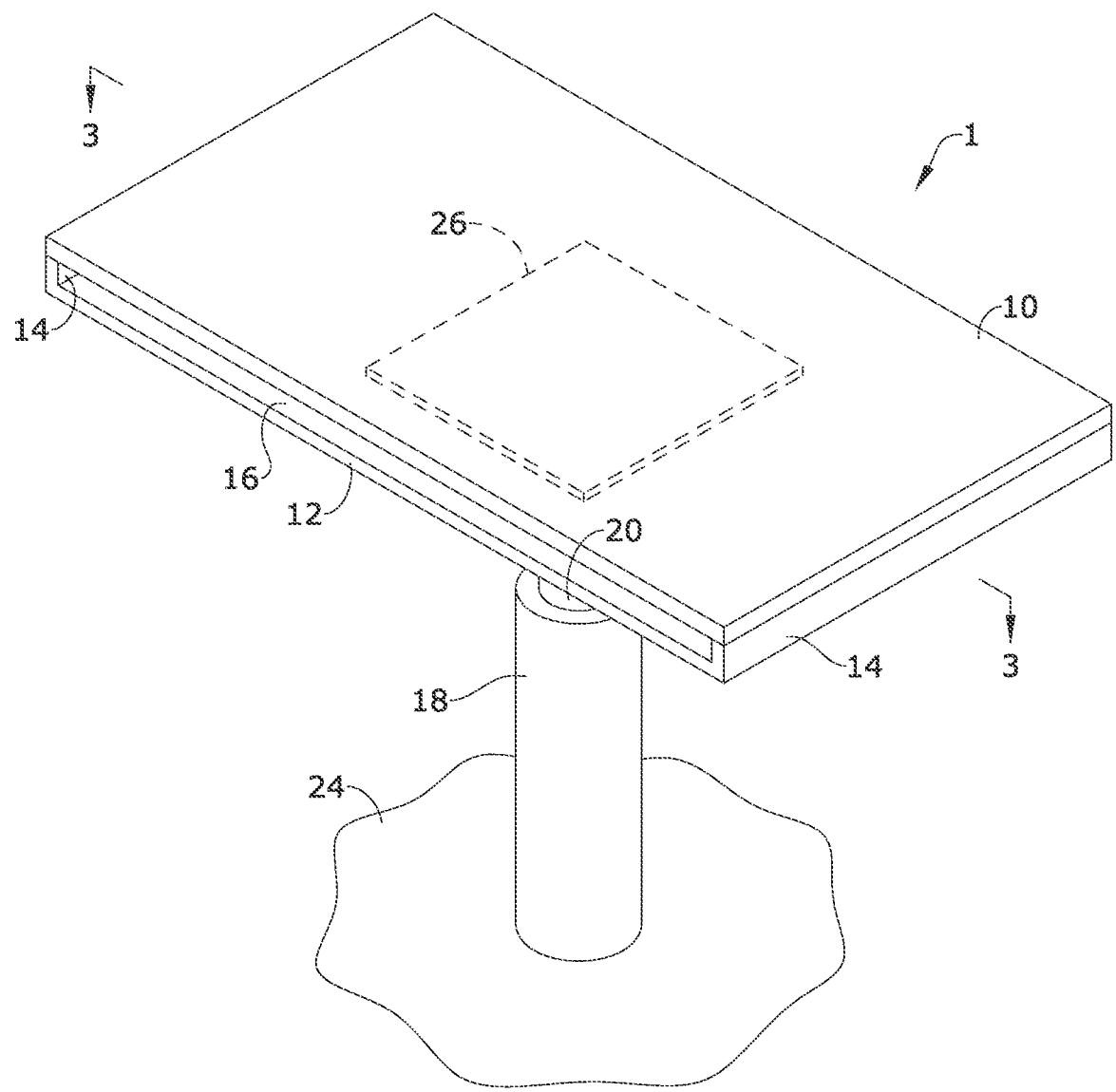
FIG. 1 is a perspective view of a medical table, in accordance with various embodiments.
Figure 2:
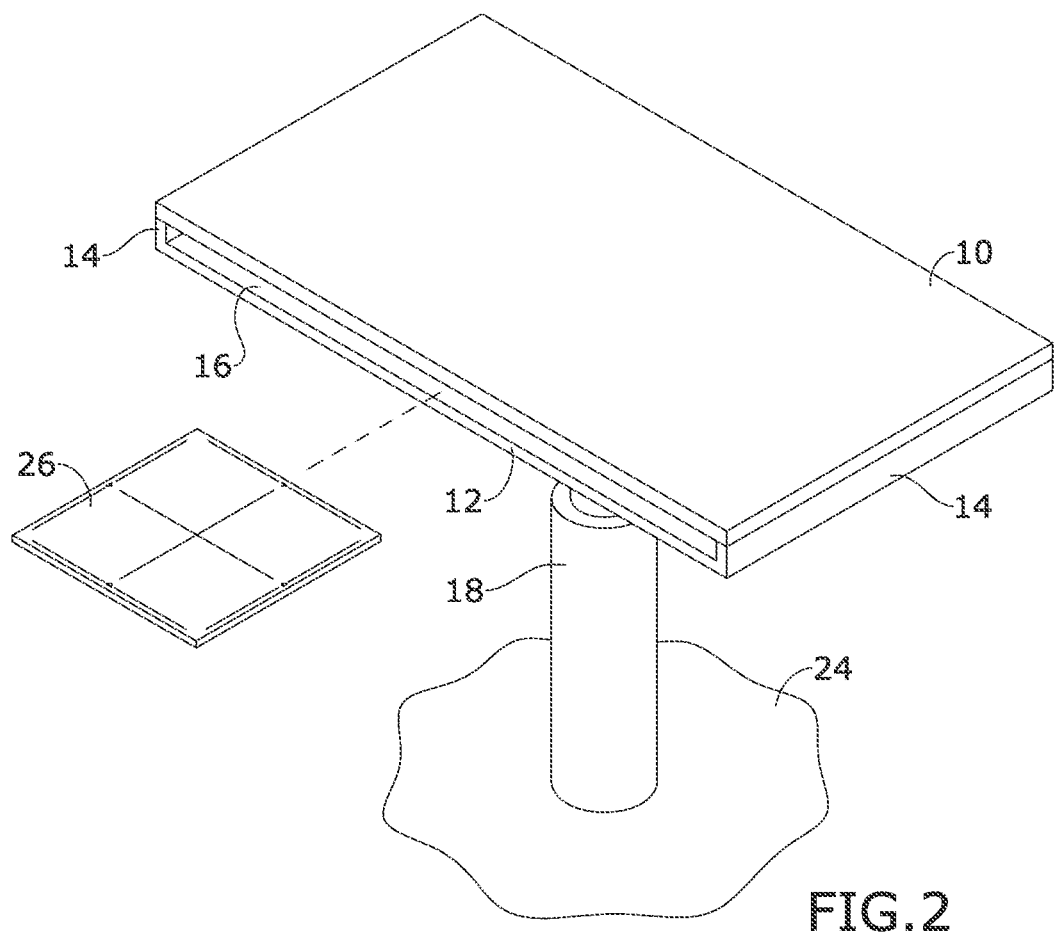
FIG. 2 is a perspective view of the medical table, showing insertion of an X-ray panel.
Figure 3:
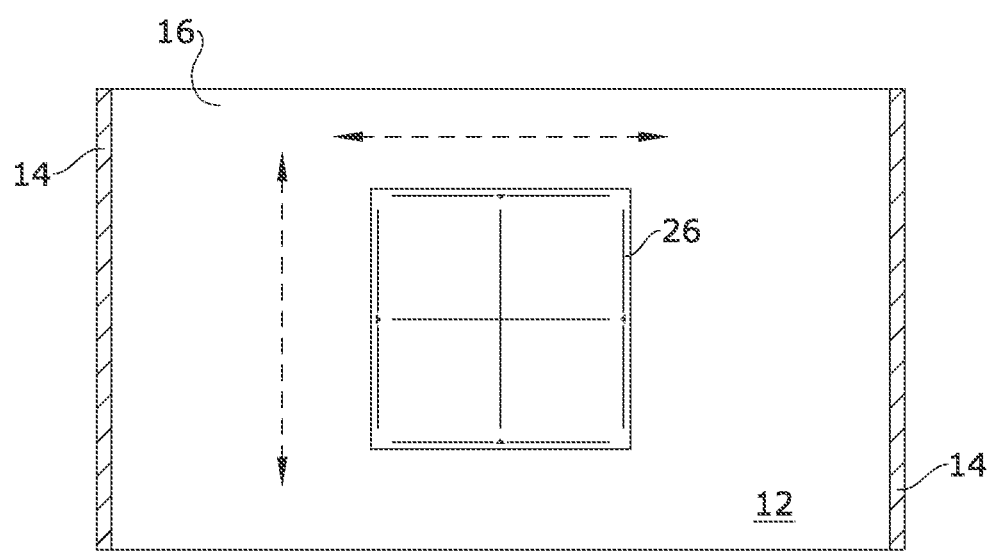
FIG. 3 is a sectional view of the medical table, taken along line 3-3 in FIG. 1, and illustrating movement of the X-ray panel to multiple positions.
Figure 4:
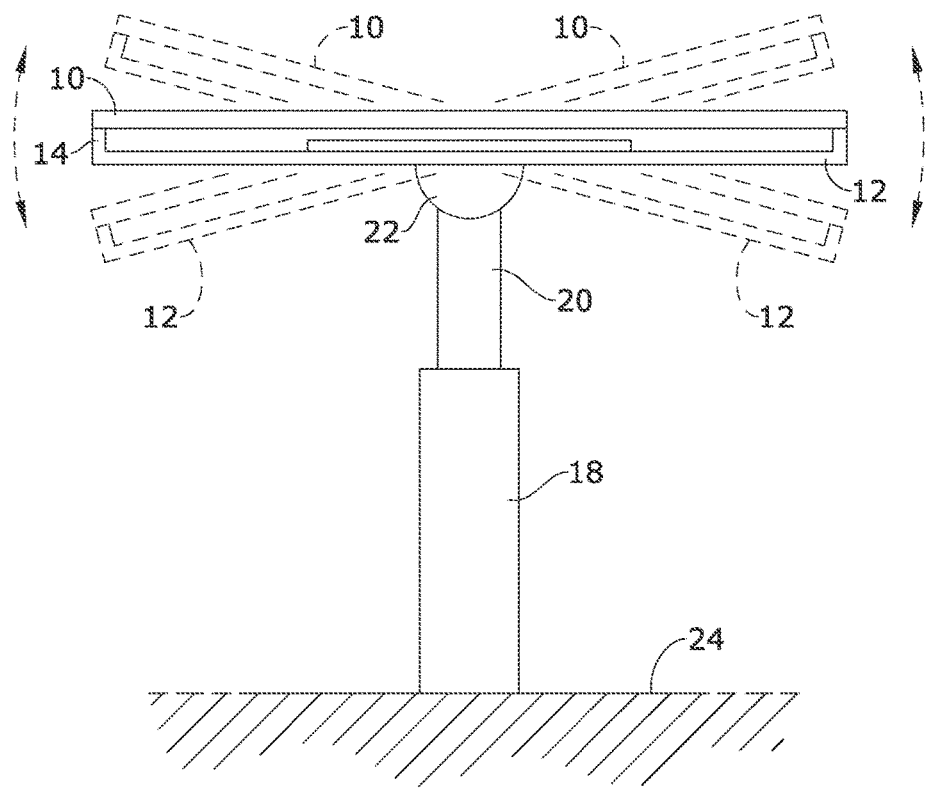
FIG. 4 is a front view of the medical table, illustrating a tilt adjustment feature of the table.
Figure 5:
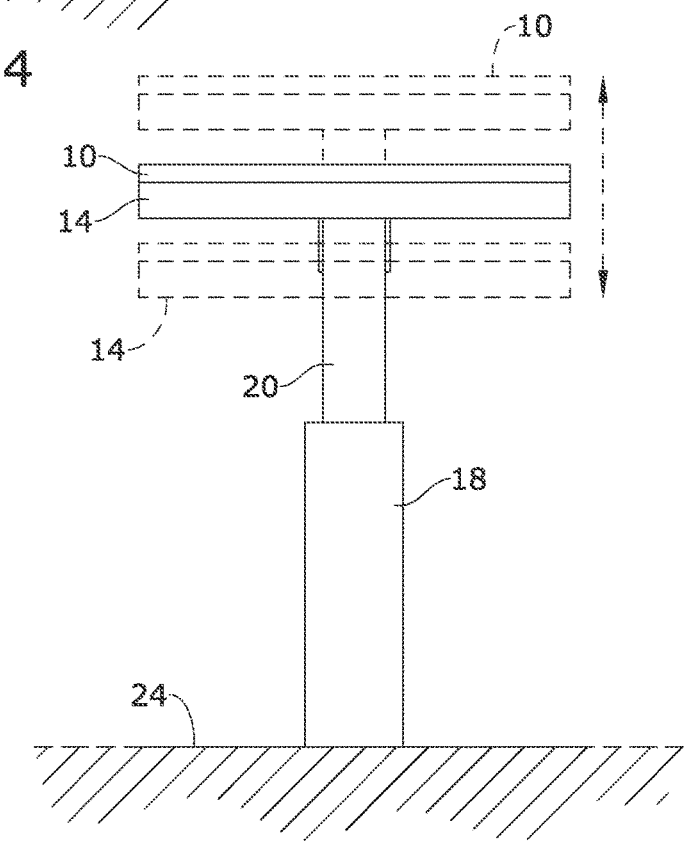
FIG. 5 is a front view of the medical table, illustrating a height adjustment feature of the table.

In the following detailed description of the invention, numerous details, examples, and embodiments of the invention are described. However, it will be clear and apparent to one skilled in the art that the invention is not limited to the embodiments set forth and that the invention can be adapted for any of several applications.

Medical procedures, including emergency and routine examinations, surgeries, and the like may utilize a c-arm X-ray device, if available, to provide imaging. In some cases, practitioners may slide an X-ray detector panel under a patient in order to obtain an X-ray image. This may require moving or repositioning the patient, which may be difficult for both the practitioner and patient and may risk injury to the patient in some cases.

The disclosed subject matter provides a system comprising a medical table 1 incorporating a radiolucent patient support surface which enables X-ray imaging of a patient supported directly on the table during a medical and/or examination procedure. In some embodiments, the disclosed system may utilize equipment which is readily available at the facility, such as an existing X-ray panel and portable X-ray source, with the disclosed medical table. The disclosed system may further enable a general exam and/or surgery table to function as an imaging table without requiring movement of the patient back and forth from a treatment/ surgery location to a dedicated X-ray imaging location.

With reference to the accompanying figures, and in accordance with various embodiments, medical table 1 may comprise an X-ray transparent support surface 10 ("tabletop") configured to support a patient (human or animal). In embodiments, X-ray transparent support surface 10 may be made, for example, of carbon fiber, solid carbon fiber, and/or polycarbonate. In certain embodiments, the entire area of X-ray transparent support surface 10 may be X-ray transparent. However, in alternate embodiments, only a portion of the area of X-ray transparent support surface 10 may be X-ray transparent, wherein X-ray transparent support surface 10 may comprise region(s) which are X-ray transparent and other region(s) which are not X-ray transparent. In further alternate embodiments, X-ray transparent support surface 10 may comprise multiple regions or panels, which may be coupled to one another.

In certain embodiments, medical table 1 may be used as a surgical table and/or an examination table. X-ray transparent support surface 10 may support the patient on its upper surface, while an X-ray detector member 26 may be placed beneath its bottom surface. In embodiments, X-ray detector member 26 may be any type of X-ray detector panel or sensor, including but not limited to imaging detectors such as photographic plates and X-ray or photographic film, various digitizing devices such as image plates or flat panel detectors, and other devices currently available or which may become available with emerging technology. Thus, an X-ray of the patient may be taken while the patient rests on X-ray transparent support surface 10, without requiring movement of the patient. The X-ray exam may be performed by radiating X-rays through the patient and X-ray transparent support surface 10 to expose X-ray detector member 26 beneath X-ray transparent support surface 10. In some embodiments, X-rays may be fired using, for example, a hand-held and/or portable X-ray unit.

Figure 6:
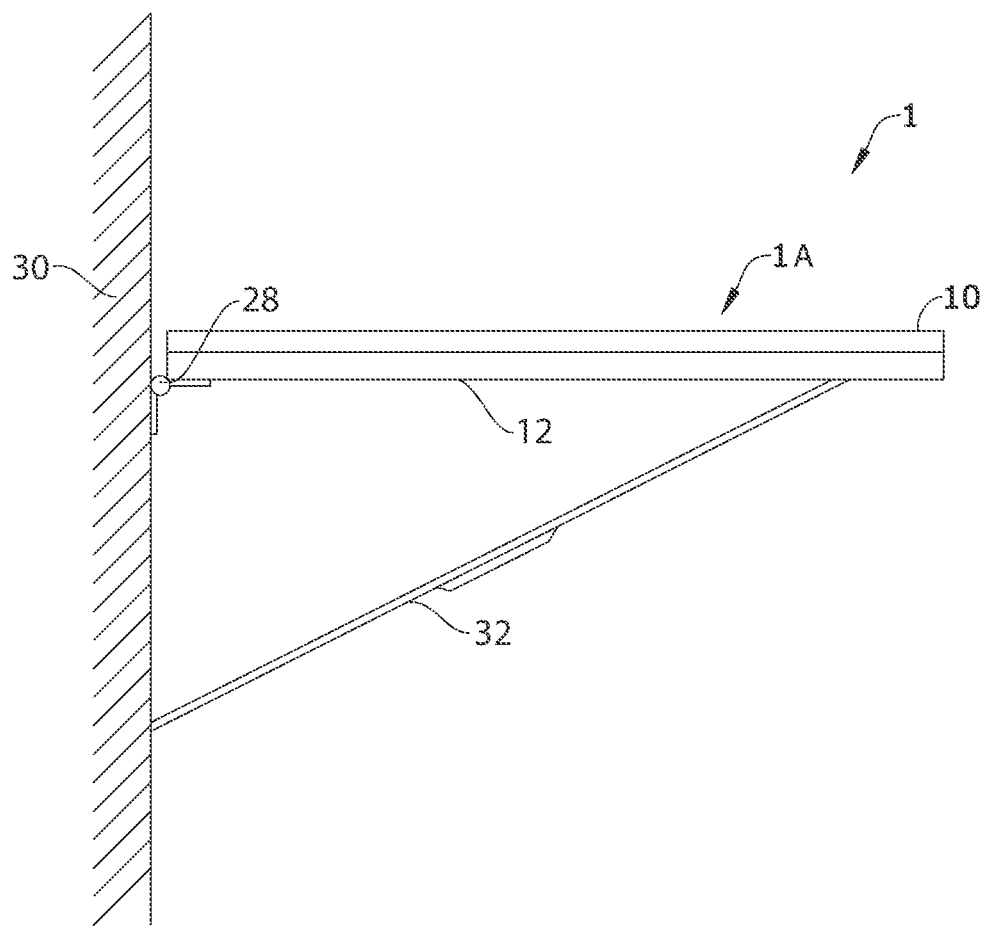
FIG. 6 is a side view of the medical table, in accordance with an alternate embodiment.

In embodiments, medical table 1 may include a detector support member 12 for support of X-ray detector member 26 beneath X-ray transparent support surface 10. In further embodiments, medical table 1 may include a table support member. In some embodiments as depicted in FIGS. 1-5, the table support member may comprise at least one support leg 18 which supports X-ray transparent support surface 10 on a ground or floor surface 24. In an alternate embodiment as depicted in FIG. 6, the table support member may comprise a wall support assembly as will be described.

In certain embodiments, detector support member 12 may be a shelf provided directly below X-ray transparent support surface 10. In some embodiments, detector support member 12 may be an integral component of medical table 1. In some embodiments, support member 12 may span approximately the entire area of X-ray transparent support surface 10, thus allowing full movement of X-ray detector member 26 anywhere under X-ray transparent support surface 10. In certain embodiments, detector support member 12 may comprise a horizontal panel connected to X-ray transparent support surface 10 via vertical side panels 14 and may be space apart from X-ray transparent support surface 10 to form an opening 16 between X-ray transparent support surface 10, side panels 14, and detector support member 12, as shown in the figures. As such, X-ray detector member 26 may be inserted through opening 16 and supported on support member 12 below X-ray transparent support surface 10 for X-raying a patient resting on X-ray transparent support surface 10. In embodiments, opening 16 may be formed on opposite sides of medical table 1, such that X-ray detector member 26 may be inserted from either side of the table. It shall be appreciated that different devices/components may be used to provide a support surface for X-ray detector member 26 in alternate embodiments. For example, in some alternate embodiments, a support table that is lower than medical table 1, and which is an independent component from the medical table, may be used for supporting X-ray detector member 26 underneath X-ray transparent support surface 10. Such support table may include wheels to enable it to be maneuvered underneath support surface 10.

In embodiments as depicted in FIGS. 1-5, table support leg 18 may be configured to support X-ray transparent support surface 10 above a ground surface 24 (e.g., hospital floor). According to an exemplary embodiment, leg 18 may be coupled to a bottom side of the support member 12, which is integrally coupled to X-ray transparent support surface 10, as shown in the figures. In some embodiments, support leg 18 may be configured to allow X-ray transparent support surface 10 to pivot, and/or rotate (see FIG. 4) about one or more axes of rotation. To this end, leg 18 may be coupled to X-ray transparent support surface 10 via pivot joint 22. In some embodiments, support leg 18 may be height adjustable. For example, leg 18 may comprise an extension 20, which may telescope from leg 18 and is coupled to X-ray transparent support surface 10. In one embodiment, extension 20 may extend from support leg 18 and may be coupled to pivot joint 22, and pivot joint 22 may be coupled to detector support member 12/X-ray transparent support surface 10, wherein support leg 18 supports medical table 1 on surface 24. Thus, leg 18, extension 20, and pivot joint 22 may together form a pivoting pedestal mount of medical table 1 which enables medical table 1 to tilt, roll, swivel, and be height adjusted. In this manner, the position of a patient supported on medical table 1 may be adjusted to a suitable working height and angle for the practitioner, for easily taking an X-ray, and for comfort of the patient. In some embodiments, leg 18 may be removable from X-ray transparent support surface 10/detector support member 12 for easy transport and relocation.

In some embodiments, medical table 1 may further comprise one or more fluid-draining channels, which may be coupled to one or more side edges of support surface 10. In embodiments, medical table 1 may comprise up to four fluid draining channels for a four-sided tabletop as depicted in the figures.

In alternate embodiments, X-ray transparent support surface 10 may comprise multiple sections which are rotationally coupled or hinged to one another. In certain embodiments, X-ray transparent support surface 10 may comprise two X-ray transparent sections which are hingedly coupled to one another, and may be positioned at an angle (e.g., up to approximately 45 degrees) with respect to one another to enable medical table 1 to recline. In one embodiment, a hinge coupling the two sections may be provided along an intermediate or approximate mid-point of the long axis of the table. This may facilitate imaging, particularly during surgery, where it may be particularly difficult to maneuver the patient and may provide more comfort to the patient. Additionally, the hinge function may enable medical table 1 to be folded up for transport (wherein leg 18 may be removed), which may be particularly useful for a mobile veterinary clinic, and/or small examination rooms. According to another embodiment, X-ray transparent support surface 10 may comprise multiple X-ray transparent sections which may be attachable and detachable to one another for compact storage and/or easy transport of the table.

It shall be appreciated that the components of medical table 1 described in several embodiments herein may comprise any alternative known materials in the field and be of any size and/or dimensions. It shall be appreciated that the components of medical table 1 described herein may be manufactured and assembled using any known techniques in the field. In one example, medical table 1 may be constructed by shaping detector support member 12 and side panels 14 from a single sheet of aluminum or stainless steel using a brake press that forms the side panels. A carbon fiber or polycarbonate top may be fitted precisely within the side panels and attached via screws that insert through holes provided within X-ray transparent support surface 10 and the top sides of side panels 14. Support member 12 may be fitted with a small electric or manual pivot component around the middle of the support member. Such pivot component may be coupled to a motorized pedestal or telescoping leg. The pivot component may be coupled to detector support member 12 by welding and to leg 18 via bolts, for example. This assembly provides a medical table which may be easily disassembled for shipping or relocation.

It shall be appreciated that the disclosed medical table 1 can have multiple configurations in different embodiments. It shall be appreciated that medical table 1 may have various support structures, including any number of legs, or no legs in alternate embodiments. For example, X-ray transparent support surface 10 and support member 12 may be used without the table support leg 18 and may be connected to a wall of a clinic or mobile medical van or supported directly on a floor. In embodiments, X-ray transparent support surface 10 and support member 12 may be attached by hinge support to the wall and held steady underneath by a metal rod while in use.

In an alternate embodiment as depicted in FIG. 6, medical table 1 may be configured as a wall table 1A configured to store vertically against a wall 30. To this end, one side of wall table 1A may be coupled via a hinge 28 to wall 30. Hinge 28 may be configured to allow the medical table to rotate between a substantially perpendicular alignment with respect to wall 30 (i.e., in level with a ground surface) when deployed for use, and to fold in parallel alignment to wall 30 for storage. In certain embodiments, a support rod 32 may be provided to hold the table in its deployed orientation. In one embodiment, support rod 32 may be lodged diagonally between wall 30 and the underside of wall table 1A, as shown. In another embodiment, a support rod may be positioned between the underside of the table and the ground or floor (i.e., in parallel alignment to the wall). In some embodiments, support rod 32 may be attached to wall table 1A or wall 30, and may be configured to rotate out for support of the table and to fold in for storage with the table. In other embodiments, rod 32 may be entirely removable when the table is folded against the wall. In some further embodiments, support rod 32 may itself be configured to fold and/or telescope between a collapsed position and an expanded position.

Wall 30 may be, for example, the wall of a room, or the wall of a vehicle such as a van. As such, medical table 1 may be ideal for use in a small room such as a veterinary clinic or urgent care facility, or for a mobile veterinary clinic, ambulance, and the like. It shall be appreciated that while wall table 1A is depicted as foldable downwards against wall 30 (wherein the underside of the table lays against the wall when folded), in alternate embodiments wall table 1A may be configured to fold upwards such that the top side of the table lies against the wall instead.

In embodiments, the disclosed subject matter may be particularly useful to the veterinary industry, as well as the medical industry. The disclosed subject matter can additionally be used in other applications, for convenient X-ray examination of any component that needs X-ray analysis. This may include non-destructive testing of drilled cores or machine parts, cadaver imaging or autopsies, and the like.

The disclosed medical table may be used for surgery and examination of a human or animal subject, whereby the X-ray detector member or detector panel can be moved, unhindered, under the entire length/body of the subject. In some embodiments, the disclosed apparatus and method enables total patient X-ray imaging without moving the patient (or anything attached to the patient such as IV tubes, monitor cables or anesthesia equipment).

The disclosed subject matter may also provide a low-cost alternative for whole body imaging during routine exam and surgery. It allows X-rays to be performed using common X-ray panels which may be available in small facilities, and may replace expensive, bulky equipment such as radiographic c-arms.

The constituent elements of the disclosed device and system listed herein are intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device. Terms such as 'approximate,' 'approximately,' 'about,' etc., as used herein indicate a deviation of within +/−10%. Relationships between the various elements of the disclosed device as described herein are presented as illustrative examples only, and not intended to limit the scope or nature of the relationships between the various elements. Persons of ordinary skill in the art may appreciate that numerous design configurations may be possible to enjoy the functional benefits of the inventive systems. Thus, given the wide variety of configurations and arrangements of embodiments of the present invention, the scope of the invention is reflected by the breadth of the claims below rather than narrowed by the embodiments described above.

What is claimed is:

1. An X-ray imaging method comprising:
providing an X-ray transparent support surface;
placing a patient on top of the X-ray transparent support surface;
placing an X-ray detector member on a detector support member beneath the X-ray transparent support surface; and
taking an X-ray of the patient by radiating X-rays through the patient and X-ray transparent support surface to expose the X-ray detector member beneath the X-ray transparent support surface,
wherein the X-ray transparent support surface is rotationally coupled to a wall via a hinge connector, and is configured to fold into the wall for storage,
wherein the detector support member comprises a horizontal panel connected to the x-ray transparent support surface via a pair of vertical side panels,
wherein the detector support member is spaced apart from the x-ray transparent support surface to form an unobstructed opening between the x-ray transparent support surface, the pair of vertical side panels, and the detector support member, said unobstructed opening extending along an entire length of the x-ray transparent support surface,
wherein the x-ray detector member can be inserted through said unobstructed opening and supported on the detector support member such that the x-ray detector member is allowed full lateral and transverse movement anywhere under x-ray transparent support surface.

2. The X-ray imaging method of claim 1, further comprising rotating the X-ray transparent support surface on the hinge connector away from the wall, and affixing the X-ray transparent support surface in a leveled position prior to placing said patient on top of the X-ray transparent support surface.

3. The X-ray imaging method of claim 1, further comprising rotating the X-ray transparent support surface on the hinge connector into the wall for storage of the –x-ray transparent support surface.

4. The X-ray imaging method of claim 1, wherein the patient is a human or animal.

5. The X-ray imaging method of claim 1, wherein the X-ray transparent support surface is a component of a medical table used for surgery and/or examination of the patient.

6. A medical table comprising:
- an X-ray transparent support surface configured to support a patient;
- a detector support member coupled to the X-ray transparent support surface and providing a shelf beneath the X-ray transparent support surface, the shelf configured to hold an X-ray detector member,
- wherein the detector support member comprises a horizontal panel connected to the X-ray transparent support surface via a pair of vertical side panels,
- wherein the detector support member is spaced apart from the X-ray transparent support surface to form an unobstructed opening between the X-ray transparent support surface, the pair of vertical side panels, and the detector support member, said unobstructed opening extending along an entire length of the X-ray transparent support surface,
- wherein the X-ray detector member can be inserted through said unobstructed opening and supported on the detector support member such that the X-ray detector member is allowed full lateral and transverse movement anywhere under X-ray transparent support surface.

7. The medical table of claim 6, further comprising at least one support leg configured to support the medical table.

8. A medical table comprising:
- an X-ray transparent support surface configured to support a patient;
- a hinge coupled to the X-ray transparent support surface, the hinge configured to pivotally couple the X-ray transparent support surface to a wall,
- a detector support member coupled to the x-ray transparent support surface and providing a shelf beneath the x-ray transparent support surface, the shelf configured to hold an x-ray detector member,
- wherein the detector support member comprises a horizontal panel connected to the x-ray transparent support surface via a pair of vertical side panels,
- wherein the detector support member is spaced apart from the x-ray transparent support surface to form an unobstructed opening between the x-ray transparent support surface, the pair of vertical side panels, and the detector support member, said unobstructed opening extending along an entire length of the x-ray transparent support surface,
- wherein the x-ray detector member can be inserted through said unobstructed opening and supported on the detector support member such that the x-ray detector member is allowed full lateral and transverse movement anywhere under x-ray transparent support surface.

* * * * *